United States Patent [19]

Koger, II et al.

[11] Patent Number: 4,552,709
[45] Date of Patent: Nov. 12, 1985

[54] PROCESS FOR HIGH-SPEED PRODUCTION OF WEBS OF DEBOSSED AND PERFORATED THERMOPLASTIC FILM

[75] Inventors: Thurman J. Koger, II, Hamilton, Ohio; Theodore E. Farrington, Jr., Milford, Me.; Eugene Weinshenker, Cincinnati, Ohio

[73] Assignee: The Procter & Gamble Company, Cincinnati, Ohio

[21] Appl. No.: 549,525

[22] Filed: Nov. 4, 1983

[51] Int. Cl.[4] ............................................. B29C 1/14
[52] U.S. Cl. ............................. 264/504; 156/244.21; 156/285; 156/498; 156/500; 425/384; 425/385; 425/387.1; 425/388
[58] Field of Search ................. 156/285, 244.21, 498, 156/500; 264/154, 155, 156, 504; 425/384, 385, 387.1, 388

[56] References Cited

U.S. PATENT DOCUMENTS

| | | | |
|---|---|---|---|
| Re. 23,910 | 12/1954 | Smith et al. | 264/555 |
| 2,776,451 | 1/1957 | Chavannes | 264/555 |
| 2,776,452 | 1/1957 | Chavannes | 425/194 |
| 2,905,969 | 9/1959 | Gilbert et al. | 264/555 |
| 3,038,198 | 6/1962 | Schaar | 15/215 |
| 3,054,148 | 9/1962 | Zimmerli | 264/92 |
| 3,685,930 | 8/1972 | Davis et al. | 425/71 |
| 3,709,647 | 1/1973 | Barnhart | 425/224 |
| 3,929,135 | 12/1975 | Thompson | 128/287 |
| 3,966,383 | 6/1976 | Bussey, Jr. et al. | 425/388 |
| 3,989,867 | 11/1976 | Sisson | 428/132 |
| 4,151,240 | 4/1979 | Lucas et al. | 264/504 |
| 4,155,693 | 5/1979 | Raley | 425/363 |
| 4,259,286 | 3/1981 | Louis et al. | 264/555 |
| 4,284,396 | 8/1981 | Thissen et al. | 425/388 |
| 4,317,792 | 3/1982 | Raley et al. | 264/504 |
| 4,342,314 | 8/1982 | Radel et al. | 128/287 |
| 4,395,215 | 7/1983 | Bishop | 425/290 |

*Primary Examiner*—Caleb Weston
*Attorney, Agent, or Firm*—E. Kelly Linman; John V. Gorman; Richard C. Witte

[57] ABSTRACT

The present invention provides a process for debossing and perforating a substantially continuous web of substantially planar thermoplastic film, using a forming structure having a patterned forming surface with holes and an opposed surface. The forming structure is open from the holes in the forming surface to the opposed surface. The forming structure moves in a direction of the length of the web of film and carries the web of film in that direction. The web of film is substantially entirely molten. A fluid differential pressure is substantially continuously applied across the thickness of the web of film from a first position along the direction of movement of the forming structure to a second position. The first and second positions are fixed relative to the moving forming structure. The fluid differential pressure is sufficiently great to cause the first surface of the web of film to be urged against the forming surface and to cause perforations to be created in the web of film. Thus a web of debossed and perforated film is formed in the image of the forming surface from the web of film. Fluid differential pressure holds the web of debossed and perforated film against the forming surface without permitting substantial spring-back of the film. Cooling fluid is applied to the second surface of the web of debossed and perforated film after the film is debossed and perforated and before the web of debossed and perforated film passes the second position. Thus the web of debossed and perforated film is cooled without permitting substantial spring-back of the film and is set by the time the web of debossed and perforated film passes the second position.

28 Claims, 7 Drawing Figures

PROCESS FOR HIGH-SPEED PRODUCTION OF WEBS OF DEBOSSED AND PERFORATED THERMOPLASTIC FILM

TECHNICAL FIELD

The present invention relates to the production of webs of perforated thermoplastic film exhibiting three-dimensional characteristics, especially to the production of such webs of film by vacuum forming at high speeds.

BACKGROUND OF THE INVENTION

Processes for embossing and for debossing and perforating heat-softened thermoplastic film are known. As used herein, a web of film is a thin sheet of thermoplastic material of definite, preferably substantially uniform, width and indefinite length. A web of embossed film is such a web of film in which numerous protuberances have been formed to provide it with a substantial third dimensional structure perpendicular to the plane of the film. A web of debossed and perforated film has protuberances which provide it a third dimensional structure perpendicular to the plane of the film in which many or all of the protuberances have holes. The protuberances of webs of embossed and of debossed and perforated film may be of a wide variety of sizes and shapes or may all be identical. Collectively such webs of embossed and debossed and perforated films are referred to herein as webs of formed film.

In processes for producing a web of formed film, a web of heat-softened film is provided on a patterned, perforated outer surface (referred to herein as a forming surface) of a structure such as an endless belt or a drum's cylindrical surface. The heat-softened film is generally pulled into conformity with the forming surface due to the presence of a vacuum on the opposite side of the forming structure and the holes in the forming surface. Whether the web of film is simply embossed or is debossed and perforated will depend on the size of the holes in the forming surface, the softness and thickness of the film being formed, the pressure differential across the film, and the time during which said pressure differential is applied.

Processes for vacuum embossing of webs of thermoplastic film are disclosed in U.S. Pat. No. Re. 23,910 issued to Smith & Smith on Dec. 12, 1954; U.S. Pat. Nos. 2,776,451 and 2,776,452 both issued to Chavannes on Jan. 8, 1957; and U.S. Pat. No. 2,905,969 issued to Gilbert & Prendergast on Sept. 29, 1959. Processes for the production of webs of debossed and perforated thermoplastic films are disclosed in U.S. Pat. No. 3,038,198 issued to Schaar on June 12, 1962; U.S. Pat. No. 3,054,148 issued to Zimmerli on Sept. 18, 1962; U.S. Pat. No. 4,151,240 issued to Lucas & Van Coney on Apr. 24, 1979; U.S. Pat. No. 4,155,693 issued to Raley on May 22, 1979; U.S. Pat. No. 4,259,286 issued to Louis, Sorensen & Ballard on Mar. 31, 1981; U.S. Pat. No. 4,317,792 issued to Raley & Adams on Mar. 2, 1982; U.S. Pat. No. 4,342,314 issued to Radel & Thompson on Aug. 3, 1982; and U.S. Pat. No. 4,395,215 issued to Bishop on July 26, 1983.

The processes disclosed in the references cited above require that the thermoplastic film be heat-softened in order to achieve the desired embossing or debossing and perforation of the film. This can be achieved as disclosed in many of the above references by heating an existing web of film above its melt temperature range such that it is in a molten state and will readily flow and attain a new configuration. Alternatively, the molten film may be achieved by feeding a web of film directly from a film extruder onto the forming surface. Such a process is disclosed in U.S. Pat. No. 3,685,930 issued to Davis & Elliot on Aug. 22, 1972, where a web of thermoplastic film is extruded directly onto the outer surface of an endless belt and a vacuum is pulled beneath the belt to make the molten web of film assume the configuration of the outer belt surface. Similarly, U.S. Pat. No. 3,709,647 issued to Barnhart on Jan. 9, 1973, discloses a web of molten thermoplastic film extruded directly onto the outer cylindrical surface of a vacuum forming drum.

In producing webs of embossed or debossed and perforated film on a patterned, perforated surface such that the film acquires a three-dimensional structure, it is generally desirable to cool the film so that its three-dimensional structure is set prior to removing the web of formed film from the forming surface. This makes the web of formed film much less susceptible to distortion of its protuberances by external forces.

A substantial amount of cooling of webs of formed film can occur by heat transfer from the film to the forming surface. In Davis and Elliott, such heat transfer is enhanced by cooling the endless belt after stripping the web of formed film from the belt and before a web of molten film is again applied to the belt. In Barnhart, a cooling medium is used inside the drum to cool the forming surface.

Cooling can also be assisted by contacting the outer film surface with an external cooling medium while the web of formed film is on the forming surface. For webs of debossed and perforated film, cooling of the formed film is usually assisted by drawing cooling air through the perforations with vacuum prior to removing the web of formed film from the forming surface; such a cooling process is disclosed, for example, in Lucas and Van Coney. Chavannes '452 discloses contacting a web of embossed film with a wet belt to cool the film. Gilbert and Prendergast discloses use of a water spray to cool a web of embossed film on the forming surface of an embossing drum.

SUMMARY OF THE INVENTION

It is an object of the present invention to provide a process for producing webs of debossed and perforated thermoplastic film at high speed.

It is a further object of the present invention to provide a process for rapidly setting webs of debossed and perforated thermoplastic film formed on a patterned forming surface in order to prevent subsequent distortions of the formed film.

It is also an object of the present invention to provide apparatus for the high-speed production of webs of debossed and perforated thermoplastic film.

The present invention provides a process for debossing and perforating a substantially continuous web of substantially planar thermoplastic film, using a forming structure having a patterned forming surface with holes and an opposed surface. The forming structure is open from the holes in the forming surface to the opposed surface. The web of film has an indefinite length, a first surface, a second surface, and a thickness which is the distance between the first and second surfaces. The film has a melt temperature range. The process comprises the steps of:

(a) providing the web of film with the first surface of the web of film proximate the forming surface of the forming structure, the forming structure moving in a direction of the length of the web of film and carrying the web of film in that direction, the web of film being substantially entirely molten;

(b) substantially continuously applying a fluid differential pressure across the thickness of the web of film from a first position along the direction of movement of the forming structure to a second position, the first and second positions being fixed relative to the moving forming structure, the fluid differential pressure being sufficiently great to cause the first surface of the web of film to be urged against the forming surface; to cause perforations to be created in the web of film, whereby a web of debossed and perforated film is formed in the image of the forming surface from the web of film, the web of debossed and perforated film having a first surface and a second surface which correspond to the first surface and the second surface, respectively, of the web of film; and to hold the web of debossed and perforated film against the forming surface;

(c) contacting the second surface of the web of film with a fluid having low heat transfer capacity for a period of time from when the web of film passes the first position through when the web of film is debossed and perforated, the web of film remaining substantially entirely molten throughout this period of time; and (d) applying cooling fluid to the second surface of the web of debossed and perforated film after it is debossed and perforated and before the web of debossed and perforated film passes the second position, such that the web of debossed and perforated film is cooled and is set by the time the web of debossed and perforated film passes the second position.

DETAILED DESCRIPTION OF THE INVENTION

Webs of debossed and perforated thermoplastic film having three-dimensional characteristics are produced according to the present invention. Debossed and perforated films can be engineered to provide a variety of configurations which will provide certain liquid handling characteristics. Such a debossed and perforated film may be used, for example, as a topsheet in an absorbent device. Such devices, including disposable diapers, incontinent pads, bandages, and the like, are disclosed in U.S. Pat. No. 3,929,135 issued to Thompson on Dec. 30, 1975. Another potential use for such debossed and perforated film is as a breatheable backsheet for a disposable absorbent device such as disclosed in U.S. Pat. No. 3,989,867 issued to Sisson on Nov. 2, 1976.

In exploring such potential uses for debossed and perforated thermoplastic film, it was determined that substantial economic advantages could be achieved if webs of such formed film could be produced at high speed, e.g., 1½–5 meters per second or faster. Such speeds would provide economies in that a single production line could produce large quantities of debossed and perforated film.

The webs of thermoplastic film prior to debossing and perforation by the processes of the present invention are substantially "planar". For purposes of clarity, the term "planar", when utilized herein to describe such webs of thermoplastic film, refers to the overall condition of the web of film when viewed by the naked eye on a macroscopic scale. In this context planar webs of film may include webs of film having fine scale surface aberrations on one or both sides. Such surface aberrations are generally not readily visible to the naked eye when the perpendicular distance between the viewer's eye and the plane of the web is about 30 cm or greater.

The present invention of a process for production of webs of debossed and perforated film at high speed is best perceived by looking at the processes for producing such webs at low speeds and understanding the difficulties encountered in trying to increase the speed of such film-forming processes.

Figure 1:
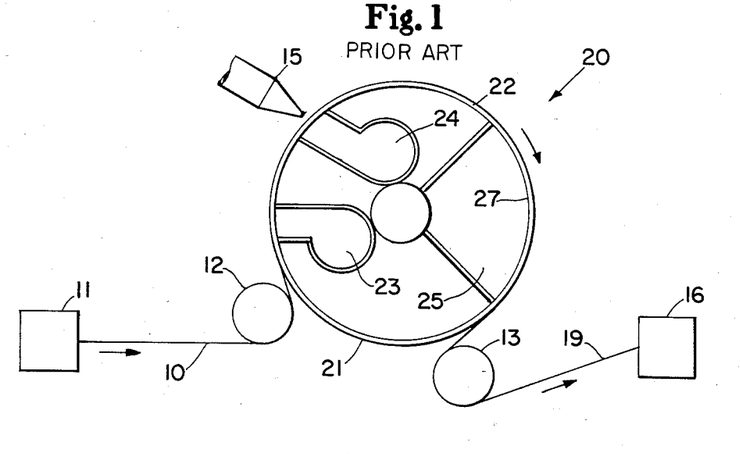
FIG. 1 is a schematic cut-away side view of a prior art process for the production of webs of debossed and perforated film.

The primary process for producing webs of debossed and perforated thermoplastic film, as disclosed in several of the references cited hereinbefore, entails the vacuum forming of a web of molten thermoplastic film. An exemplary vacuum film-forming process is disclosed in Lucas and Van Coney cited hereinbefore. FIG. 1 is a schematic representation of a process disclosed in Lucas and Van Coney. Vacuum debossing and perforation of web of substantially planar thermoplastic film 10 is accomplished by the use of vacuum film-forming drum 20.

The cylindrical surface of drum 20 is covered by forming structure 22 having patterned forming surface 21 and opposed surface 27. Forming surface 21 has a surface configuration desired to be imparted to web of film 10. Forming surface 21 contains holes, and forming structure 22 is open from the holes in forming surface 21 to opposed surface 27 such that fluid can pass through forming structure 22. Examples of forming structures which can be used on vacuum forming drums, and can be used to produce debossed and perforated films according to the processes of the present invention, and supporting structures for such forming structures are disclosed in Lucas and Van Coney; Radel and Thompson; Bishop; commonly assigned allowed patent application of William I. Mullane entitled METHOD AND APPARATUS FOR UNIFORMLY DEBOSSING AND APERTURING A RESILIENT PLASTIC WEB, Ser. No. 230,488, filed Feb. 2, 1981, now U.S. Pat. No. 4,441,952; and commonly assigned patent application of William I. Mullane entitled UNIFORMLY DEBOSSING AND APERTURING A MOVING PLASTIC WEB USING STATIONARY SUPPORT MEMBER IN FORMING AREA, Ser. No. 542,796, filed on Oct. 17, 1983; all of which are hereby incorporated by reference.

Lucas and Van Coney, in a preferred embodiment, discloses a process for forming a web of thermoplastic film exhibiting a regulated pattern of tapered capillaries as generally disclosed in Thompson cited hereinbefore. Such a process is depicted in FIG. 1. Web of substantially planar thermoplastic film 10 is supplied from any conventional means 11 around idler roll 12 to forming surface 21 of tubular forming structure 22 of vacuum film-forming drum 20. Vacuum film-forming drum 20 has a plurality of independently adjustable levels of vacuum which influence circumferentially spaced sections of the web of film through forming structure 22 from vacuum chambers 23, 24, and 25 within drum 20. A curtain of hot air is directed radially inwardly toward a predetermined zone of drum 20 from hot air supply jet 15 to flash heat web of film 10 above its melt temperature range to a molten state so that it can be debossed and perforated. Vacuum applied from within drum 20 through vacuum chamber 24 acts in concert with the curtain of hot air from jet 15 to effect debossing and perforating of web of film 10 as it travels on forming surface 21 of forming structure 22 between hot air jet 15 and vacuum chamber 24 (the debossing/perforating position). Thus web of debossed and perforated film 19 is produced from web of film 10. Web of formed film 19 is taken off forming drum 20, around roll 13, and is accumulated by any conventional means 16.

Tension in web of film 10 may be controlled upstream of the debossing/perforating position by the influence of a vacuum in vacuum chamber 23 on web of film 10. Tension in web of formed film 19 downstream from the debossing/perforating position can be controlled through the influence of a vacuum in vacuum chamber 25 on web of formed film 19. Vacuum chamber 25 can also aid in the cooling of web of formed film 19 by drawing cooling air through the perforations of web of formed film 19.

Figure 2:
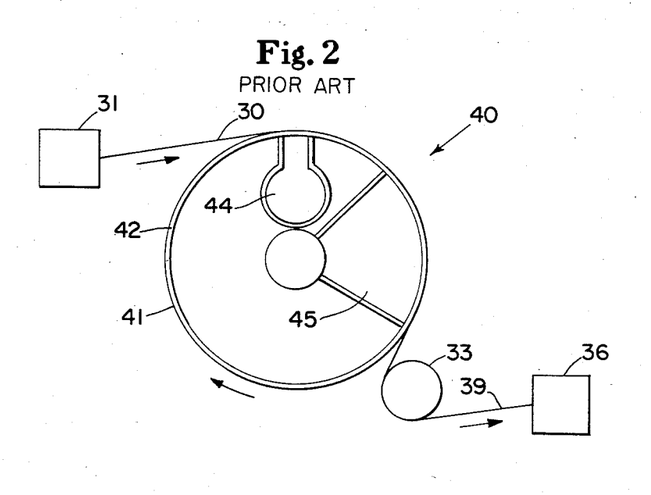
FIG. 2 is a schematic cut-away side view of a modified process similar to that shown in FIG. 1.

FIG. 2 depicts an alternate process for vacuum debossing and perforating a web of thermoplastic film with subsequent air cooling. Web of film 30 is provided on forming surface 41 of forming structure 42 on vacuum film-forming drum 40 at a temperature above its melt temperature range and in a molten state. Source 31 of web of film 30 may be any means of providing such a molten web of film, for example, a conventional film extruder. Web of film 30 is debossed and perforated as it passes over vacuum chamber 44 thus producing web of formed film 39. Web of debossed and perforated film 39 is cooled to a temperature below its melt temperature range and web of formed film 39 is set in its new configuration prior to removing it from forming surface 41 of forming structure 42. This cooling of web of formed film 39 is achieved by heat transfer from web of formed film 39 to forming structure 42 and by drawing cooling air through the perforations of web of formed film 39 with vacuum chambers 44 and 45. Web of formed film 39 is taken off forming drum 40 around roll 33, and is accumulated by any conventional means 36.

The thermoplastic materials from which webs of debossed and perforated films may be produced according to the present invention, have characteristic rheological properties which depend on their composition and temperature. Below their glass transition temperature, such thermoplastic materials are quite hard and stiff and often brittle. Below this glass transition temperature, the molecules are in rigid, fixed positions. Above the glass transition temperature but below the melt temperature range the thermoplastic material generally has a certain degree of crystallinity, and is generally flexible and to some degree deformable under a force. Such a thermoplastic has an elasticity that is dependent on the rate of deformation, length of time it is deformed, and its temperature.

The melt temperature range of a thermoplastic material is the temperature at which its crystalline volume elements are in equilibrium with the molten state. Virtually all thermoplastic materials melt over a temperature range rather than at a specific temperature due to variations in molecular structure, molecular weight distribution, and crystalline properties. Above the melt temperature range, thermoplastic polymers are in their molten state and behave as non-Newtonian fluids, that is, their viscosity is dependent on shear rate. These molten polymers exhibit elastic qualities. When they are deformed in shear or in tension, they tend to spring back to the shape they had before deformation. The degree of elasticity exhibited depends on several factors including temperature of the molten polymer, rate of shear or extension of the molten polymer, and extent of shear or extension. A simplified explanation of the cause of the elastic behavior of molten polymers is that shear and extension forces tend to stretch out and untangle the long molecular chains of the thermoplastic material. When the shearing or tensioning force is removed, the molecules relax and reentangle, causing the polymer to spring back. Under a low rate of shear or extension, a molten polymer exhibits little elasticity since the molecular chains have time to move relative to each other without stretching. Under a high rate of shear or extension, a molten polymer may exhibit substantial elasticity. Therefore, the thermo/mechanical process which a molten polymer is subjected to determines the molten polymer's elastic properties. For complex thermo/mechanical polymer processes, very limited data is available for prediction of elastic behavior. These complex cases arise when strain rates are very high, when strain rates are non-uniform, and when simultaneous heat transfer is involved.

In the process shown in FIG. 2, web of thermoplastic film 30 has an average temperature above the melt temperature range of the film and is substantially entirely molten when web of film 30 is debossed and perforated by the vacuum pulled by vacuum chamber 44. When the process shown in FIG. 2 (and, similarly, that shown in FIG. 1) is run at relatively low drum speeds, the film appears to exhibit little elasticity as it is drawn into the shape of forming surface 41 by vacuum from vacuum chamber 44; once the film is drawn into the shape of forming surface 41, little or no retraction of the protuberances is observed.

It has been found that as the drum speed of such processes is increased, a certain speed is reached where, although the film is debossed and apertured completely while exposed to the vacuum from vacuum chamber 44, the protuberances of the formed film will tend to retract toward their initial configuration, and the protuberances will be reduced in size and their perforations may reclose. Thus at this certain speed it becomes apparent that the film-forming process is operating in a range where the elastic characteristics of the molten polymer are very pronounced. While the present invention is not limited to this mechanism, it is believed that this elastic behavior of the formed film is not exhibited below this certain speed because, at such lower speeds, there is sufficient heat transferred from web of formed film 39 to forming structure 42 and the air drawn through web of formed film 39 to set web of formed film 39 before it leaves the influence of vacuum chamber 44. Because of the limited knowledge concerning the complex thermo-mechanical polymer processes occurring during the debossing, perforation, and cooling of the web of film, the speed at which retraction of the protuberances will occur is not predictable from slow-speed operation. This certain speed at which such protuberance retraction is encountered will vary substantially depending on the type of polymer, its thickness and its temperature profile.

The present invention provides processes for overcoming the deficiencies of the prior art processes of FIGS. 1 and 2 so that a web of film can be debossed and perforated at high speed without experiencing substantial retraction of the protuberances or closing of the perforations. In processes of the present invention, a web of molten thermoplastic film is debossed and perforated against a forming surface by a fluid differential pressure, and is held substantially continuously by fluid differential pressure against that forming surface until it is cooled sufficiently by a cooling fluid to set the web of formed film in its new configuration. As used herein, a film is "set" when it has solidified sufficiently to substantially hold its configuration without the aid of an external force. The time needed to set a molten formed film depends on the temperature to which the film is cooled. The fluid differential pressure which holds the molten formed film against the forming surface may be from a single source or may have multiple sources. It is preferred that the fluid differential pressure be achieved by vacuum from a single vacuum chamber. However, the fluid differential pressure may be achieved by vacuum, gas pressure, liquid pressure, or a combination thereof. A substantially continuous web of substantially planar thermoplastic film is debossed and perforated according to the present invention using a perforated forming structure having a patterned forming surface and an opposed surface with holes, the forming structure being open from the holes in the forming surface to the opposed surface. The web of film has an indefinite length, a first surface, and a second surface, and a thickness, the thickness being the distance between the first surface and the second surface.

The web of film is provided with the first surface of the web of film proximate the forming surface. The structure moves in a direction of the length of the web of film. The web of film is substantially entirely molten. In order to ensure that the web of film is entirely molten, it is preferred that the web of film be at a temperature above its melt temperature range. Fluid differential pressure is applied substantially continuously across the thickness of the web of film from a first position along the direction of movement of the forming structure to a second position. The first and second positions are fixed relative to the moving forming structure. The fluid differential pressure across the thickness of the web of film is sufficiently great to cause the first surface of the web of film to be urged against the forming surface and to cause perforations to be created in the web of film. Thus a web of debossed and perforated film is formed in the image of the forming surface from the web of film. The web of debossed and perforated film has a first surface and a second surface which correspond to the first surface and the second surface, respectively, of the web of film. Fluid differential pressure is continued to be applied across the thickness of the web of debossed and perforated film to hold it against the forming surface to prevent the protuberances from retracting and the perforations from closing.

During the period of time from when the web of film passes the first position through when the web of film is debossed and perforated, the second surface of the web of film is in contact with a fluid having low heat transfer capacity, preferably air. By having such a low heat transfer capacity fluid contacting the web of film, it remains substantially entirely molten throughout this period of time. By keeping the web of film molten, the web of film is readily debossed and perforated and will hold its new configuration if the spring-back tendency of the molten film is overcome. The spring-back tendency of the molten film is overcome by applying cooling fluid to the second surface of the web of debossed and perforated film after it is debossed and perforated and before it passes the second position where the application of the fluid differential pressure ceases. In this manner, the web of debossed and perforated film is cooled and is set in its new configuration by the time the web of debossed and perforated film passes the second position.

Thus processes of the present invention use two fundamental steps in producing a web of debossed and perforated thermoplastic film. The debossing and perforation of the film occurs under the influence of a fluid differential pressure across the thickness of the film while the film is in a molten state, and the fluid in contact with the film has low heat transfer capacity to ensure that the film remains substantially entirely molten until it is debossed and perforated. Then while continuing to hold the film in its new configuration with the fluid differential pressure, a cooling fluid is used to rapidly cool the film (preferably to a temperature below its melt temperature range) and to set the web of debossed and perforated film in its new configuration.

Figure 3:
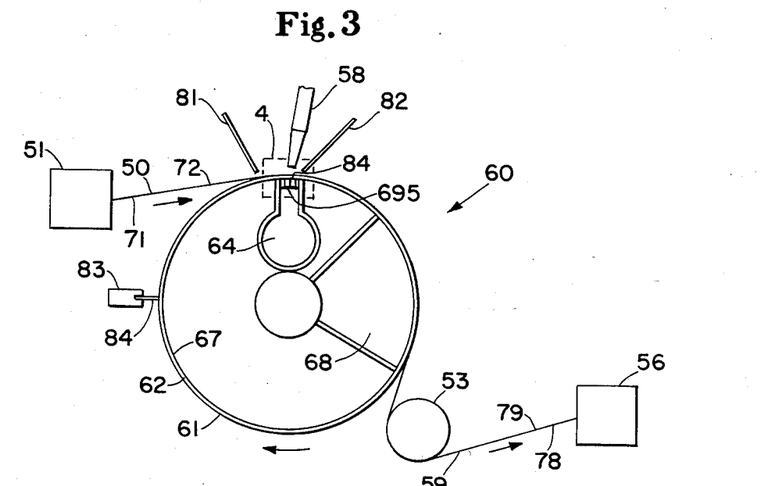
FIG. 3 is a schematic cut-away side view of a process for the production of webs of debossed and perforated thermoplastic film according to the present invention.

A preferred process of the present invention is depicted schematically in FIG. 3. Substantially continuous web of substantially planar thermoplastic film 50 is provided on a patterned, perforated forming surface 61 of vacuum film-forming apparatus 60. Web of film 50 is preferably a web of thin film having a substantially uniform cross-machine direction width (perpendicular to the plane of FIG. 3) and an indefinite machine direction length (generally from left to right in FIG. 3).

Web of film 50 is comprised of thermoplastic material which may be a pure thermoplastic substance, mixtures of thermoplastic substances, or a mixture of thermoplastic substances with other components. Preferred thermoplastic materials used to produce webs of formed film according to the processes of the present invention include materials normally cast as films such as polyolefins, nylons, polyesters, and the like. Especially preferred thermoplastic materials formed by processes of the present invention are low density polyethylenes, linear low density polyethylenes, high density-low density polyethylene blends, ethylene-vinylacetate copolymers, and other copolymers and blends containing a substantial fraction of these materials.

Substantially continuous web of substantially planar thermoplastic film 50 is provided on film-forming apparatus 60 preferably at an average temperature above the melt temperature range of the film; more preferably at least about 90° C. above the melt temperature range of the film; more preferably still at least about 140° C. above the melt temperature range of the film, so that web of film 50 is substantially entirely molten.

Web of film 50 has first surface 71, second surface 72, and a small thickness which is the distance between first surface 71 and second surface 72. For economic reasons, a thin formed film is preferred for most purposes. The thickness of web of film 50 when it reaches its forming position above opening 84 of vacuum chamber 62 is preferably no more than about 0.25 mm, more preferably no more than about 0.1 mm, more preferably still the film thickness is from about 0.015 mm to about 0.06 mm,, most preferably the thickness is about 0.025 mm.

Web of film 50 is provided on film-forming apparatus 60 at a temperature above its melt temperature range so that web of film 50 is substantially entirely molten (a forming temperature) by any conventional means 51. An existing web of film may be preheated and fed to apparatus 60, or may be fed to apparatus 60 at a lower temperature and heated to its forming temperature while on apparatus 60 such as with hot air jets as disclosed in Lucas and Van Coney and described hereinbefore. A preferred method for providing web of film 50 to film-forming apparatus 60 at a forming temperature is to provide a molten web of film directly from a film extruder. Any conventional film extruding apparatus can be used for such purpose.

Web of film 50 is provided at a forming temperature on patterned, perforated forming surface 61 of tubular forming structure 62 of film-forming apparatus 60. Forming structure 62 moves in a direction of the length of web of film 50 (clockwise in FIG. 3) and carries web of film 50 in that direction. Although such a process of the present invention can be run at a low speed, its advantage over the prior art processes is that it can be used for high-speed production of debossed and perforated thermoplastic film. It is therefore preferred that the linear speed of forming surface 61 be about 1½ m/sec. or faster, more preferably about 2½ m/sec. or faster, more preferably still about 3½ m/sec. or faster.

A sufficiently great vacuum is applied to web of film 50 through forming surface 61 to cause web of film 50 to be urged against forming surface 61 and to be perforated. Web of film 50 is thereby debossed and perforated in the image of forming surface 61, thus forming web of formed (debossed and perforated) film 59. Web of formed film 59 is taken off forming drum 60, around roll 53, and is accumulated by any conventional means 56. Web of formed film 59 has first surface 78 and second surface 79 which correspond to first surface 71 and second surface 72, respectively, of web of film 50.

Film-forming apparatus 60 can be an apparatus which uses the forming surface of a forming structure such as the outer surface of an endless belt or the outer cylindrical surface of a drum to provide the forming surface on which the film is formed. Preferred film-forming apparatus and forming structures are disclosed in the aforementioned incorporated references: Lucas and Van Coney, Radel and Thompson, Bishop, and the two patent applications of Mullane.

Figure 4:
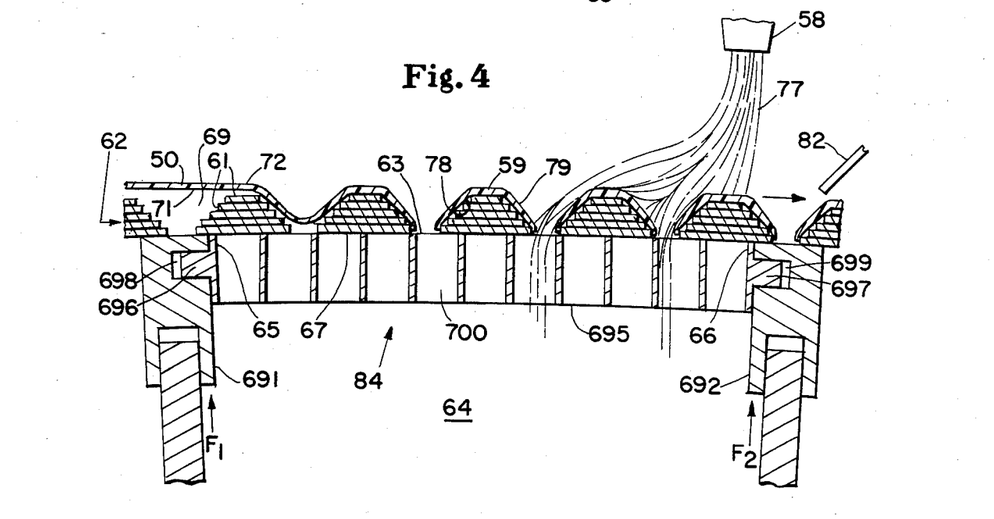
FIG. 4 is a detailed schematic view of area 4 of FIG. 3.
Figure 5:
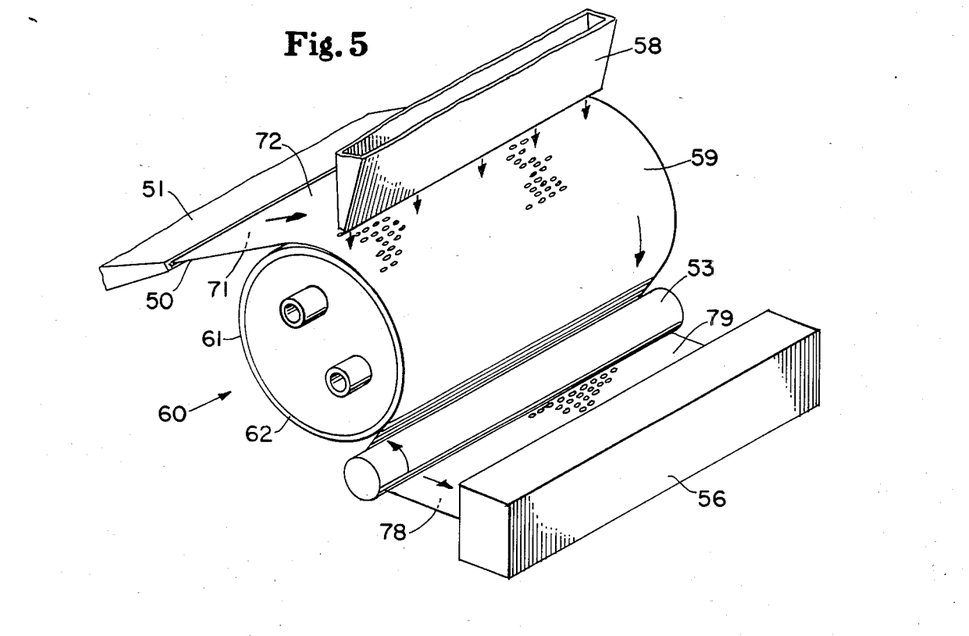
FIG. 5 is a perspective view of the process shown in FIG. 3.

A preferred film-forming process of the present invention can be achieved using the apparatus depicted schematically in FIG. 3. FIG. 5 is a perspective view of the film-forming apparatus shown in FIG. 3. Vacuum film-forming drum 60 has, as its tubular outer layer, forming structure 62 which has patterned forming surface 61. Forming structure 62 can be produced with many different forming surface patterns as disclosed in the references cited hereinbefore. FIG. 4 provides a more detailed cross-sectional view of forming structure 62 of FIG. 3 which is made as taught by Radel and Thompson. Forming structure 62 shown in FIG. 4 is used to produce a web of formed film exhibiting a regular pattern of tapered capillaries as disclosed in Thompson cited hereinbefore. Forming structure 62 has a forming surface 61 with holes 63 and opposed surface 67. Forming surface 61 includes the entire surface against which web of film 50 is urged during the film forming operation; for forming structure 62 depicted in FIG. 4, forming surface 61 includes the land areas between the conical depressions and the conical surfaces of the depressions. Forming structure 62 is open from holes 63 in forming surface 61 to opposed surface 67.

Web of molten film 50 is provided with first surface 71 against forming surface 61 of forming structure 62 which is rotating clockwise in FIG. 3. A vacuum from a vacuum source, such as vacuum chamber 64, is continuously applied to opposed surface 67 of forming structure 62 from a first position at edge 65 of opening 84 of vacuum chamber 64 along the direction of movement of forming structure 62 to a second position at edge 66 of opening 84 of vacuum chamber 64. These positions are fixed proximate opposed surface 67 of forming structure 62 which continually moves past these positions. The vacuum thus applied is sufficiently great to cause first surface 71 of web of film 50 to be urged against forming surface 61 and to cause perforations to be created in web of film 50. The vacuum from vacuum chamber 64 being applied from opposed surface 67 of forming structure 62 through holes 63 causes molten web of film 50 to flow into conical depressions 69 and into contact with the conical surfaces of forming surface 61, and then to perforate at holes 63 in forming surface 61. Thus web of film 50 is debossed and perforated in the image of forming surface 61. The vacuum needed to deboss and perforate web of film 50 depends on many factors including the composition, thickness, and temperature of web of film 50; the rotating speed of forming structure 62; and the distance between edges 65 and 66 of opening 84 of vacuum chamber 64.

Forming structure 62 is generally quite thin and flexible. (The thickness of forming structure 62 is exaggerated in FIGS. 3 and 4.) When travelling over opening 84 of vacuum chamber 64, forming structure 62 may require additional support to prevent it from flexing into opening 84 of vacuum chamber 64. Attempts to make forming structure 62 more rigid and inflexible has resulted in supporting structures which at least partially block some of holes 63 in forming surface 61. Such partial blockage of holes 63 often results in an unperforated protuberance in formed film debossed and perforated on such a forming structure. Therefore, it is preferred that forming structure 62 be constructed such that there is no partial blockage of any of holes 63. Where this results in a thin, flexible forming structure 62, it is preferred that a stationary support member such as that disclosed in co-pending patent application of William I. Mullane entitled UNIFORM DEBOSSING AND APERTURING A MOVING PLASTIC WEB USING STATIONARY SUPPORT MEMBER IN FORMING AREA cited hereinbefore be used to support forming structure 62 at opening 84 of vacuum chamber 64. Support member 695 provides this support function.

Support member 695 is preferably constructed in the following manner. Support member 695 comprises a substantially rigid honeycomb structure having hexagonally-shaped openings 700. Support member 695 extends substantially all the way across opening 84 of vacuum chamber 64 in both the machine and cross-machine directions, thereby providing continuous machine direction and cross-machine direction support to forming structure 62 during its traverse of opening 84 of vacuum chamber 64. Hexagonally shaped openings 700 are so sized and oriented that every hole 63 in forming surface 61 of forming structure 62 will at some point in its traverse of stationary support member 695 be fully exposed to the vacuum of vacuum chamber 64. Support member 695 is preferably supported by means of arcuate projections 696 and 697 which engage arcuate grooves 698 and 699 on wear strips 691 and 692, respectively. The arcuate shape of the projections and mating grooves permits outward and inward movement of support member 695 in a radial direction. To provide uniform support to opposed surface 67 of forming structure 62, yet allow for disturbances occurring during the processing operation, e.g., weld seams in forming structure 62, wear strips 691 and 692 are preferably biased against opposed surface 67 of forming structure 62 by means of forces $F_1$ and $F_2$ respectively. In a particularly preferred embodiment, forces $F_1$ and $F_2$ are equal, and are provided by means of hydraulic or pneumatic cylinders which are controlled by means of a common pressure regulator in order to maintain a constant force between opposed surface 67 of forming structure 62 and the outermost surface of support member 695. Alternatively, support member 695 can be held in a stationary position and forming structure 62 be allowed to flex under the influence of vacuum from vacuum manifold 64 until opposed surface 67 of forming structure 62 rides on support member 695.

As will be appreciated by those skilled in the art, the particular pattern of apertures employed in support member 695 is non-critical. Rather, it is the relationship between the size, configuration and frequency of the apertures in support member 695 and the size, configuration and frequency of holes 63 in forming surface 61 of forming structure 62 which is controlling, i.e., hole 63 in forming surface 61 must at some points during their traverse of support member 695 be fully exposed to the vacuum from vacuum chamber 64, yet support member 695 must provide sufficient support to opposed surface 67 of forming structure 62 that forming structure does not deform excessively during its traverse of opening 84 of vacuum chamber 64.

A fluid having low heat transfer capacity, preferably ambient air, is in contact with second surface 72 of web of film 50 until after web of film 50 is debossed and perforated. Thus web of film 50 remains substantially entirely molten and preferably at an average temperature above the melt temperature range of the film until after it is debossed and perforated. After perforation of the film has occurred, ambient air is drawn through the perforations of web of debossed and perforated film 59 by the vacuum in vacuum chamber 64; this holds web of debossed and perforated film 59 against forming surface 61 and forces the protuberances of web of formed film 59 to retain their new configuration.

Stationary vacuum chamber 64 is constructed and positioned proximate opposed surface 67 of forming structure 62, such that a vacuum can be drawn substantially continuously on each of holes 63 of forming surface 61 while each such hole moves from a first position proximate first edge 65 of opening 84 of vacuum chamber 64 to a second position proximate second edge 66 of opening 84 of vacuum chamber 64. Process costs for the film-forming operation of the present invention are dependent to a large extent on the vacuum capacity needed for the process. The vacuum capacity needed for a given film-forming operation is approximately proportional to the distance between edges 65 and 66 of opening 84 of vacuum chamber 64. Thus it is desirable to minimize the distance between edges 65 and 66. Edges 65 and 66 of opening 84 of vacuum chamber 64 are located along the direction of movement (machine direction) of forming structure 62. Edges 65 and 66 are preferably no more than about 15 cm apart, more preferably no more than about 10 cm apart, more preferably still from about 1 cm to about 5 cm apart.

In order to set web of debossed and perforated film 59 such that it permanently retains its new configuration, the film is rapidly cooled by flowing a cooling fluid through web of formed film 59 and through holes 63 of forming surface 61 and through forming structure 62 while the film is between first edge 65 and second edge 66 of opening 84 of vacuum chamber 64. Web of formed film 59 is preferably cooled in this manner such that its average temperature is below its melt temperature range. Vacuum is preferably applied through forming structure 62 and web of formed film 59 substantially continuously from the time of forming of web of formed film 59 until the film is set in its new configuration, and preferably until the temperature of web of formed film 59 is below the melt temperature range of the film. The film is set in its new configuration if there is substantially no retraction of its protuberances when no fluid differential pressure is applied across the thickness of web of formed film 59.

The preferred method of cooling molten, debossed and perforated web of formed film 59 is by applying a cooling fluid to second surface 72 of web of formed film 59. The cooling fluid is preferably a cooling liquid, more preferably cooling water 77. Cooling water 77 is applied to second surface 72 of web of formed film 59 between first edge 65 and second edge 66 of opening 84 of vacuum chamber 64 after web of formed film 59 has been formed. Cooling water 77 is drawn through the perforations of web of formed film 59 and through holes 63 in forming surface 61 and through forming structure 62 with vacuum from chamber 64. In this manner, web of formed film 59 is cooled and is set by the time web of formed film 59 passes by second edge 66 of opening 84 of vacuum chamber 64.

Cooling water 77 can be applied to second surface 79 of web of formed film 59 in any manner such as through nozzle 58 as an intermittent or continuous sheet of water which may be pressure or gravity fed, as a spray, or other manner. Cooling water 77 is preferably applied through nozzle 58 under pressure as a substantially continuous, thin sheet of water. Cooling water may also be applied to second surface 79 of web of formed film 59 by dipping forming structure 62 carrying web of formed film 59 into a bath of cooling water after debossing and perforation has occurred.

Nozzle 58 is positioned such that cooling water 77 can be applied to second surface 79 of web of formed film 59 only after debossing and perforation has occurred. If any cooling water 77 is applied to web of film 50 prior to debossing and perforation, e.g. by splashing or otherwise, the film is generally set such that it will not become debossed and perforated in the image of forming surface 61.

In the preferred process shown in FIG. 3, a low vacuum is preferably drawn on web of formed film 59 through forming structure 62 by vacuum chamber 68; this helps control tension in web of formed film 59 downstream from the debossing/perforating position and also removes water from web of formed film 59. Residual heat in web of formed film 59 also helps dry the formed film by vaporizing residual moisture from web of formed film 59. Web of formed film 59 is preferably dried substantially entirely by vacuum removal of water and air flow past and through web of formed film 59 while on forming structure 62, and residual heat in web of formed film 59.

If only a portion of web of formed film 59 is being debossed and perforated, cooling fluid is preferably applied to the unformed regions of the film to cool such regions below the melt temperature range of the film prior to removing web of formed film 59 from forming surface 61 of forming structure 62. Such cooling of unformed regions of web of formed film 59 is preferably achieved by spraying cooling water on such regions while web of formed film 59 is over vacuum chamber 68. Vacuum chamber 68 helps hold web of formed film 59 on forming surface 61 so that it does not shift under the influence of such cooling water spray, and also may help remove the cooling water from web of formed film 59. Web of formed film 59 is taken off forming drum 60, around roll 53, and is preferably dried and then accumulated by any conventional means 56.

Baffle 81 if preferably placed proximate second surface 72 of web of film 50 near edge 65 of opening 84 of vacuum chamber 64. Baffle 82 is preferably placed proximate and second surface 79 of web of formed film 59 near edge 66 of opening 84 of vacuum chamber 64. Such placement of baffles 81 and 82 prevents a substantial air flow along second surface 72 of web of film 50 and second surface 79 of web of film 59 away from opening 84 of vacuum chamber 64. Without such baffles and prevention of such air flow, fluttering and shifting of web of film 50 and web of formed film 59 sometimes occurs. Baffle 81 also can be positioned so that it acts as a splash shield to prevent cooling water 77 from splashing on web of film 50 prior to debossing and perforation.

A preferred method of applying cooling water 77 to second surface 79 of web of formed film 59 is to form a pool of cooling water on second surface 79 which can be drawn through the perforations of web of formed film 59 and holes 63 in forming surface 61 by vacuum from vacuum chamber 64. Such a pool of cooling water can be achieved, for example, in the process shown in FIG. 4 by putting a rubber edge on baffle 82 so that the rubber edge rides on second surface 79 of web of formed film 59 and keeps most of the cooling water from flowing past baffle 82. The pool of water is thus contained in a V-shaped pool bounded by the sloping, moving forming structure 62 and baffle 82. The pool of water is fed by nozzle 58. Care must be taken to insure that the pool of water contacts web of formed film 59 only after debossing and perforation has been completed.

If excess cooling water remains on forming surface 61 at the time web of film 50 contacts forming surface 61, web of film 50 may be cooled below the melt temperature range of the film prior to debossing and perforation of the film. Therefore, it is preferred to have excess moisture wiped from forming surface 61 after web of formed film 59 is removed from forming surface 61 and before web of film 50 contacts forming surface 61. An exemplary unit which can be used for such purpose is shown in FIG. 3; it comprises rubber wiping blade 84 which is mounted in rigid holder 83. Rubber wiping blade 84 is placed against forming surface 61 of forming structure 62 so that it wipes excess moisture from forming surface 61.

EXAMPLES

The following examples are presented as illustrations of the present invention; they are not intended to limit the scope of the invention in any way.

EXAMPLE 1

A web of debossed and perforated film is made substantially by the process depicted in FIGS. 3 and 4 and disclosed hereinbefore, with forming structure 62 being replaced by forming structure 240 which imparts a different image to the formed film. A fragmentary portion of forming structure 240 used to produce the web of formed film is shown in perspective view in FIG. 6. Such a forming structure can be made as disclosed in Radel and Thompson. The pattern of forming surface 241 of forming structure 240 consists of a repeated pattern of nested pentagonal depressions 141 with land area 151 between the depressions. Forming surface 241 consists of land area 151 and the sidewalls of pentagonal depressions 141 which are substantially perpendicular to land area 151 and extend through forming structure 240 to opposed surface 242, thus forming pentagonal holes in forming surface 241. The open area in forming surface 241 created by these pentagonal holes is about 67% of the projected surface area of forming structure 240. Dimension A across all ribs of land area 151 between parallel sides of adjacent pentagons is about 0.178 mm. Each pentagon has one side B about 0.477 mm long and the other four sides about 0.651 mm long. Each pentagon has two 90° angles C which are never adjacent angles and are always formed by two of the equal length sides of the pentagon. Dimension D which is the thickness of forming structure 240 is about 1.3 mm. Forming structure 240 has an outer diameter of about 29 centimeters and is made from stainless steel. It is driven such that the linear speed of forming surface 241 is about 2½ meters per second.

A web of molten film is provided to forming structure 240 directly from a conventional film extrusion setup. Two single screw extruders are used to feed one linear die having a 0.64 mm gap about 30 cm wide. Both extruders are NRM Pacemaker 111 models available commercially from NRM Corporation, Tallmadge, Ohio. Each extruder has a 6.35 cm diameter screw and a length:diameter ratio of 24:1. The screws, general purpose polyolefin screws with a 2.5:1 compression ratio, are also commercially available from NRM Corporation. The film is extruded horizontally and the distance from the extrusion die to the surface of the forming structure is about 15 cm.

Figure 6:
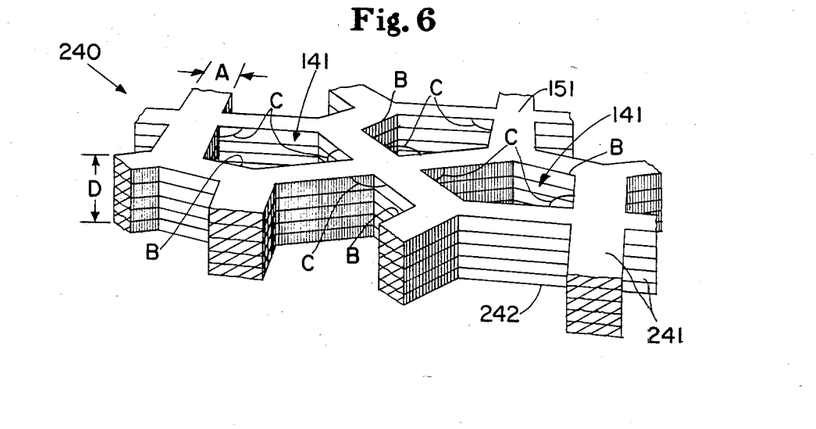
FIG. 6 is a fragmentary enlarged, partially exploded, perspective view of an exemplary laminate forming structure used to produce debossed and perforated thermoplastic film according to the present invention.

The polymer used to produce the formed film is a low density polyethylene, Petrothene NA 344 available commercially from U.S. Industrial Chemicals Corp., New York, N.Y. The polymer has a melt temperature range of about 93° C.–110° C. The film is extruded at a die temperature of about 260° C. The film as extruded is thicker than desired and is drawn down to the desired thickness due to the fact that the linear speed of forming surface 241 of forming structure 240 is faster than the linear speed of the extruded web of film. The web of film is extruded at a speed such that its thickness at the forming position over opening 84 of vacuum chamber 64 is about 0.025 mm.

The length (machine direction) of opening 84 of vacuum chamber 64 beneath forming structure 240 at the forming position is about 3.0 cm. The width (cross-machine direction) of opening 84 of vacuum chamber 64 is about 15 cm and is about centered on the web of film. A vacuum from vacuum chamber 64 beneath forming structure 240 is such that the fluid pressure differential across the thickness of the film is about 440 mm Hg.

Cooling water 77 is applied from pressurized linear slot nozzle 58 to the debossed and perforated film about in line with second edge 66 of opening 84 of vacuum chamber 64. The temperature of cooling water 77 as applied is about 17° C. The distance from the bottom of linear slot nozzle 58 to the surface of the formed film is about 1.3 cm. The thin slot opening of nozzle 58 is about 0.5 mm. The pressure of cooling water 77 is set to achieve a desired flow rate of water from linear nozzle slot 58. The flow rate of cooling water 77 is about 0.012 liter/sec/cm of nozzle width (cross-machining direction).

A web of formed film was produced having substantially the pattern of forming surface 241 of forming structure 240. Cooling water sprayed on the unformed sides of the web of formed film after the formed film passes nozzle 58. The basis weight of the formed film produced is about 23.3 g/m$^2$.

EXAMPLE 2

A web of debossed and perforated thermoplastic film is produced in the same manner as in Example 1 with the following differences. The thermoplastic polymer used to produce the web of formed film is a 30/70 blend of low density polyethylene and linear low density polyethylene. The low density polyethylene is the same as used in Example 1. The linear low density polyethylene is Dowlex 2047 available commercially from the Dow Chemical Company, Midland, Mich. The melt temperature range of Dowlex 2047 is about 106° C–127° C. The distance from the bottom of cooling water nozzle 58 to the surface of the formed film is set at about 3.8 cm. The flow rate of cooling water is set at about 0.0075 liter/sec/cm of nozzle width. The length (machine direction) of opening 84 of vacuum manifold 64 is about 2.5 cm.

A formed film is produced having substantially the configuration of forming surface 241 of forming structure 240. The basis weight of the formed film produced is about 23.3 g/m$^2$.

EXAMPLE 3

A web of debossed and perforated film is produced in the same manner as in Example 1 with the following differences. Forming structure 240 is driven at a speed such that the linear speed of forming surface 241 is about 3½ m/sec. The film is extruded at a speed such that its thickness at the forming position is about 0.018 mm. A vacuum from vacuum chamber 64 is such that the fluid pressure differential across the thickness of the web of film is about 430 mm Hg. The flow rate of cooling water 77 is set at about 0.020 liter/sec/cm of nozzle width.

A formed film is produced having substantially the configuration of forming surface 241 of forming structure 240. The basis weight of the formed film produced is about 15.9 g/m$^2$.

EXAMPLE 4

A web of debossed and perforated thermoplastic film is produced in the same manner as in Example 1 with the following differences. Forming structure 240 is driven at a speed such that the linear speed of forming surface 241 is about 1½ m/sec. The film is extruded at a speed such that its thickness at the forming position is about 0.058 mm. The length (machine direction) of opening 84 of vacuum chamber 64 is set at about 4.1 cm.

A formed film is produced having substantially the same configuration as forming surface 241 of forming structure 240. The basis weight of the formed film produced is about 52.5 g/m$^2$.

EXAMPLE 5

Figure 7:
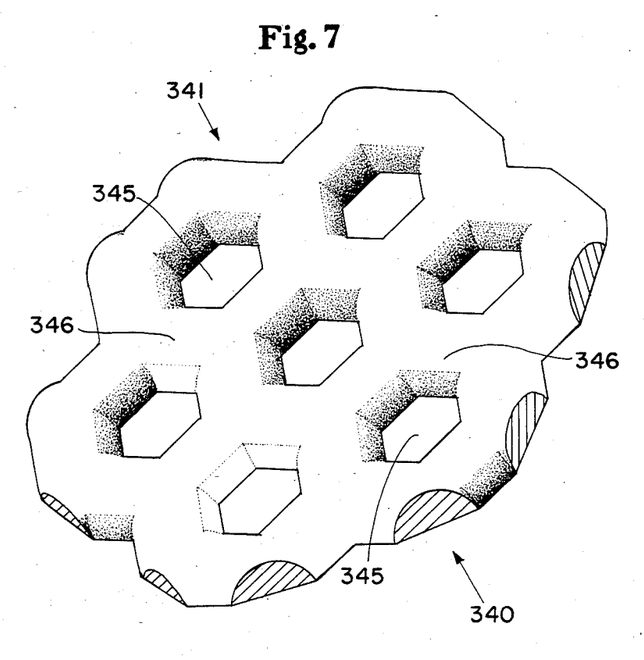
FIG. 7 is a fragmentary enlarged, perspective view of another exemplary forming structure used to produce debossed and perforated thermoplastic film according to the present invention.

A web of debossed and perforated film is produced in the same manner as in Example 1 with the following differences. Forming structure 340 shown in fragmentary, perspective view in FIG. 7 is used in forming the film. Forming structure 340 has forming surface 341 which is a repeating pattern with regular hexagonal holes 345 about 0.64 mm across (between parallel sides of the hexagon). Portions 346 of forming surface 341 between adjacent sides of hexagonal holes 345 are half cylinders having a radius of about 0.38 mm. Hexagonal holes 345 provide an open area in forming surface 341 of about 40% of the projected surface area of forming structure 340. A nickel screen having the configuration shown in FIG. 7 from which forming structure 340 was made is available commercially from Stork Screens America, Inc., Charlotte, North Carolina. The screen is designated type 25H screen—25 mesh/hexagonal holes/91.4 cm repeat/300 microns thick.

The length (machine direction) of opening 84 of vacuum chamber 64 is set at about 2.5 cm. A vacuum from vacuum chamber 64 is such that the fluid pressure differential across the web of film is about 480 mm Hg. The width (cross-machine direction) of opening 84 of vacuum chamber 64 is set at about 50 cm. The extruder die width is set at about 60 cm. The distance from the bottom of cooling water nozzle 58 to the surface of the formed film is set at about 3.8 cm.

A formed film is produced having substantially the same configuration as forming surface 341 of forming structure 340. The basis weight of the formed film produced is about 23.3 g/m$^2$.

While particular embodiments of the invention have been illustrated and described, it would be obvious to those skilled in the art that various changes and modifications can be made without departing from the spirit and scope of the invention. It is intended to cover, in the appended claims, all such modifications that are within the scope of this invention.

What is claimed is:

1. A process for debossing and peforating a substantially continuous web of substantially planar thermoplastic film, using a forming structure having a patterned forming surface with holes and an opposed surface, said forming structure being open from said holes in said forming surface to said opposed surface, said web of film having an indefinite length, a first surface, a second surface, and a thickness, said thickness being the distance between said first surface and said second surface, said film having a melt temperature range, which process comprises the steps of:

(a) providing said web of substantially planar film with said first surface of said web of film proximate said forming surface, said forming structure moving in a direction of said length of said web of film and carrying said web of film in said direction, said web of film being substantially entirely molten;

(b) substantially continuously applying fluid differential pressure across said thickness of said web of film from a first position along said direction of movement of said forming structure to a second position, said first and second positions being fixed relative to said moving forming structure, said fluid differential pressure being sufficiently great to cause said first surface of said web of film to be urged against said forming surface; to cause perforations to be created in said web of film, whereby a web of debossed and perforated film is formed in the image of said forming surface from said web of film, said web of debossed and perforated film having a first surface and a second surface which correspond to said first surface and said second surface, respectively, of said web of substantially planar film; and to hold said web of debossed and perforated film against said forming surface without permitting substantial spring-back of said web of film;

(c) contacting said second surface of said web of film with a fluid having low heat transfer capacity for a period of time from when said web of substantially planar film passes said first position through when said web of film is debossed and perforated, said web of film remaining substantially entirely molten throughout said period of time; and (d) applying cooling fluid to said second surface of said web of debossed and perforated film after said period of time and before said web of debossed and perforated film passes said second position, such that said web of debossed and perforated film is cooled and is set without permitting substantial spring-back of said web of debossed and perforated film by the time said web of debossed and perforated film passes said second position.

2. The process of claim 1 wherein said low heat transfer capacity fluid is a gas and said cooling fluid is a liquid.

3. The process of claim 2 wherein said gas is air.

4. The process of claim 3 wherein said liquid is water.

5. The process of claim 2 wherein said thermoplastic film is selected from the group consisting of low density polyethylene, linear low density polyethylene, high density-low density polyethylene blends, ethylene-vinylacetate copolymers and other copolymers and blends containing a substantial fraction of these materials.

6. The process of claim 4 wherein in step (d) said web of debossed and perforated film is cooled to an average temperature below said melt temperature range by the time said web of debossed and perforated film passes said second position, wherein in step (a) said web of film is at an average temperature above said melt temperature range, and wherein in step (c) said web of film remains at an average temperature above said melt temperature range throughout said period of time.

7. A process for debossing and perforating a substantially continuous web of substantially planar thermoplastic film, using a forming structure having a patterned forming surface with holes and an opposed surface, said forming structure being open from said holes in said forming surface to said opposed surface, said web of film having an indefinite length, a first surface, a second surface, and a thickness, said thickness being the distance between said first surface and said second surface, said film having a melt temperature range, which process comprises the steps of:

(a) providing said web of substantially planar film with said first surface of said web of film proximate said forming surface, said forming structure moving in a direction of said length of said web of film and carrying said web of film in said direction, said web of film being substantially entirely molten;

(b) substantially continuously applying a vacuum from a vacuum source to said opposed surface of said forming structure from a first position along said direction of movement of said forming structure to a second position, said first and second positions being fixed proximate said opposed surface of said moving forming structure whereby said opposed surface continually moves past said first and second positions, said vacuum being sufficiently great to cause said first surface of said web of film to be urged against said forming surface; to cause perforations to be created in said web of film, whereby a web of debossed and perforated film is formed in the image of said forming surface from said web of substantially planar film, said web of debossed and perforated film having a first surface and a second surface corresponding to said first surface and said second surface, respectively, of said web of substantially planar film; and to hold said web of debossed and perforated film against said forming surface without permitting substantial spring-back of said debossed and peforated film; and (c) applying cooling fluid to said second surface of said web of debossed and perforated film and drawing said cooling fluid through said perforations of said web of debossed and perforated film and through said holes in said forming surface with said vacuum, such that said web of debossed and perforated film is cooled and is set without permitting substantial spring-back of said web of debossed and perforated film by the time said web of debossed and perforated film passes said second position.

8. The process of claim 7 wherein said cooling fluid is a cooling liquid.

9. The process of claim 8 wherein said cooling liquid is water.

10. The process of claim 8 wherein said cooling liquid is applied under pressure as a substantially continuous, thin sheet of liquid.

11. The process of claim 8 wherein said cooling liquid is applied by dipping said web of debossed and perforated film into a bath of said cooling liquid.

12. The process of claim 8 wherein said cooling liquid is applied by forming a pool of said cooling liquid on said second surface of said web of debossed and perforated film.

13. The process of claim 8 wherein said web of film in step (a) is at an average temperature of at least about 90° C. above said melt temperature range.

14. The process of claim 8 wherein said web of film is carried by said forming structure at a linear speed of about 1½ m/sec. or faster.

15. The process of claim 8 wherein said web of film is carried by said forming structure at a speed of about 2½ m/sec. or faster.

16. The process of claim 8 wherein said web of film is carried by said forming structure at a speed of about 3½ m/sec. or faster.

17. The process of claim 8 wherein said thermoplastic film is selected from the group consisting of low density polyethylene, linear low density polyethylene, high density-low density polyethylene blends, ethylene-vinylacetate copolymers and other copolymers and blends containing a substantial fraction of these materials.

18. The process of claim 17 wherein said film thickness is from about 0.015 mm to about 0.06 mm.

19. The process of claim 8 wherein said cooled web of debossed and perforated film is dried substantially entirely by vacuum removal of water and air flow past and through said web of formed film while on said forming structure, and residual heat in said web of formed film.

20. The process of claim 8 wherein said web of debossed and perforated film is cooled to an average temperature below said melt temperature range by the time said web of debossed and perforated film passes said second position.

21. The process of claim 18 wherein said web of debossed and perforated film is cooled to an average temperature below said melt temperature range by the time said web of debossed and perforated film passes said second position.

22. An apparatus for debossing and perforating a substantially continuous web of thermoplastic film having an indefinite length, said apparatus comprising:
   (a) a forming structure having a patterned forming surface with holes and an opposed surface, said forming structure being open from said holes in said forming surface to said opposed surface;
   (b) means for moving said forming structure in a direction of said length of said web of film;
   (c) a stationary vacuum manifold, said manifold being constructed and positioned proximate said opposed surface of said forming structure, such that a vacuum can be drawn substantially continuously on each of said holes of said forming surface while said each hole moves from a first position proximate a first edge of said vacuum manifold to a second position proximate a second edge of said vacuum manifold along said direction of movement of said forming structure; and
   (d) means for applying a cooling fluid to said forming surface of said forming structure between said first edge and said second edge of said vacuum manifold, said means for applying said cooling fluid being positioned such that said cooling fluid can be applied to said web of film only after said web of film is debossed and perforated.

23. The apparatus of claim 22 wherein said first position and said second position are from about 1 cm to about 5 cm apart along said direction of movement of said forming structure.

24. The apparatus of claim 22 wherein said forming surface is a cylindrical surface of a forming drum.

25. The apparatus of claim 22 wherein said forming surface is a surface of an endless belt.

26. The apparatus of claim 22 wherein said means for applying cooling fluid applies a thin sheet of liquid under pressure.

27. The apparatus of claim 22 wherein said means for applying cooling fluid is a bath of cooling liquid into which said forming structure is dipped.

28. The apparatus of claim 22 wherein said means for applying cooling fluid provides a pool of cooling liquid on said forming surface.

* * * * *

UNITED STATES PATENT AND TRADEMARK OFFICE
CERTIFICATE OF CORRECTION

PATENT NO. : 4,552,709

DATED : November 12, 1985

INVENTOR(S) : Thurman J. Koger, II, Theodore E. Farrington, Jr. and Eugene Weinshenker It is certified that error appears in the above-identified patent and that said Letters Patent is hereby corrected as shown below:

Column 5, line 44, "of", third occurrence, should read -- for --.

Column 11, line 37, "betwen" should read -- between --.

Column 18, line 31, Claim 7, "peforated" should read -- perforated --.

Signed and Sealed this

Fourth Day of February 1986

[SEAL]

Attest:

Attesting Officer

DONALD J. QUIGG

Commissioner of Patents and Trademarks